US010426802B2

(12) United States Patent
Sakamoto et al.

(10) Patent No.: US 10,426,802 B2
(45) Date of Patent: Oct. 1, 2019

(54) METHOD FOR PRODUCING SHEET-SHAPED CELL CULTURE (71) Applicant: TERUMO KABUSHIKI KAISHA, Shibuya-ku, Tokyo (JP)

(72) Inventors: Kenta Sakamoto, Sagamihara (JP); Kouichirou Yori, Kanagawa (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 0 days.

(21) Appl. No.: 14/943,161

(22) Filed: Nov. 17, 2015

(65) Prior Publication Data

US 2016/0067284 A1 Mar. 10, 2016

Related U.S. Application Data (63) Continuation of application No. PCT/JP2014/063058, filed on May 16, 2014.

(30) Foreign Application Priority Data

May 17, 2013 (JP) .................................. 2013-105204

(51) Int. Cl.
*A61K 35/34* (2015.01)
*C12N 5/071* (2010.01)
*A61K 35/28* (2015.01)
*C12N 5/077* (2010.01)
*C12N 5/0775* (2010.01)

(52) U.S. Cl.
CPC .............. *A61K 35/34* (2013.01); *A61K 35/28* (2013.01); *C12N 5/0602* (2013.01); *C12N 5/0657* (2013.01); *C12N 5/0658* (2013.01); *C12N 5/0662* (2013.01)

(58) Field of Classification Search
None
See application file for complete search history.

(56) References Cited

U.S. PATENT DOCUMENTS

| | | | |
|---|---|---|---|
| 5,145,770 A * | 9/1992 | Tubo | A01N 1/02 424/574 |
| 2007/0238173 A1 | 10/2007 | Yamagami et al. | |
| 2008/0038821 A1 | 2/2008 | Tachaboonyakiat et al. | |
| 2008/0226692 A1 | 9/2008 | Sato et al. | |
| 2009/0053277 A1 | 2/2009 | Nagaya et al. | |
| 2014/0072599 A1 | 3/2014 | Kinooka et al. | |
| 2016/0067284 A1 | 3/2016 | Sakamoto et al. | |

FOREIGN PATENT DOCUMENTS

| | | |
|---|---|---|
| GB | 2 416 777 A | 2/2006 |
| JP | 2005-229869 A | 9/2005 |
| JP | 2007-528755 A | 10/2007 |
| JP | 2008-22715 A | 2/2008 |
| JP | 2008136420 A | 6/2008 |
| JP | 2009219376 A | 1/2009 |
| JP | 2009-082005 A | 4/2009 |
| JP | 2010-81829 A | 4/2010 |
| JP | 210-226991 A | 10/2010 |
| JP | 2011115058 A | 6/2011 |
| JP | 2011-224398 A | 11/2011 |
| JP | 2011229508 A | 11/2011 |
| JP | 2012-235731 A | 6/2012 |
| JP | 5634646 B | 10/2014 |
| WO | 2005-011524 A1 | 2/2005 |
| WO | 2005/035734 A1 | 4/2005 |
| WO | 2006/038427 A1 | 4/2006 |
| WO | WO 2006/080434 A1 | 8/2006 |
| WO | 2006/093151 A1 | 9/2006 |
| WO | WO 2012/118099 A1 | 9/2012 |

OTHER PUBLICATIONS

Kenichi et al. JP 2010-081829 machine translated by EPO.*
Sigma-Aldrich "Resuscitation of frozen cell lines" Fundamental Techniques in Cell Culture Laboratory Handbook—2nd Edition, available online from company's webpage << http://www.sigmaaldrich.com/technical-documents/protocols/biology/resuscitation-of-frozen.html>>, copyright 2010.*
Extended European Search Report dated Oct. 27, 2016 by the European Patent Office in corresponding European Patent Application No. 14797732.6 (9 pages).
Yu-Shuan Chen et al., "Poly(N-isopropylacrylamide) hydrogels with interpenetrating multiwalled carbon nanotubes for cell sheet engineering", Biomaterials, vol. 34, No. 30, 2013, pp. 7328-7334.
Yi Hong et al., "Light-induced cell detachment for cell sheet technology," Biomaterials, vol. 34, No. 1, 2013, pp. 11-18.
Nakagami, H., et al., "Adipose Tissue-Derived Stromal Cells as a Novel Option for Regenerative Cell Therapy", Journal of Atherosclerosis and Thrombosis, vol. 13, No. 2, pp. 77-81, 2006.
Haraguchi, Y., et al., "Concise Review: Cell Therapy and Tissue Engineering for Cardiovascular Disease", Stem Cells Translational Medicine, vol. 1, No. 2, pp. 136-141, 2012.
Ohashi, K., et al., "Production of Islet Cell Sheets Using Cryopreserved Islet Cells", Transplantation Proceedings, vol. 43, No. 9, pp. 3188-3191, Nov. 2011.
Yokomuro, H., et al., "Cryopreserved Human Heart Cell Transplantation-Effect of Cryopreservation on Cell Proliferation and Immunogenicity", vol. 107, No. 3 , pp. 150-157, 2006.

(Continued)

*Primary Examiner* — Emily A Cordas
(74) *Attorney, Agent, or Firm* — Buchanan Ingersoll & Rooney PC (57) ABSTRACT

A sheet-shaped cell culture and method for producing a sheet-shaped cell culture are disclosed having a high activity such as high cytokine productivity and a production method thereof. The method for producing a sheet-shaped cell culture can include freezing cells, thawing the frozen cells and forming a sheet-shaped cell culture. A sheet-shaped cell culture which is produced by the production method and which has a high activity and a method for treating a disease associated with an abnormality of a tissue with the sheet-shaped cell culture.

13 Claims, 4 Drawing Sheets

(56) References Cited

OTHER PUBLICATIONS

Yokomuro, H., et al., "Effect of Cryopreservation on Cell Proliferation and Immunogenicity of Transplanted Human Heart Cells", Annals of Thoracic and Cardiovascular Surgery, vol. 16, No. 2, pp. 105-112, 2010.
International Search Report (PCT/ISA/210) dated Aug. 19, 2014, by the Japanese Patent Office as the International Searching Authority for International Application No. PCT/JP2014/063058.
Office Action (Notification of Reasons for Refusal) dated Dec. 12, 2014, by the Japanese Patent Office in corresponding Japanese Patent Application No. 2014-208847, and an English translation of the Office Action. (7 pgs).
Office Action (Notification of Reasons for Refusal) dated Feb. 3, 2015, by the Japanese Patent Office in corresponding Japanese Patent Application No. 2014-208847, and an English translation of the Office Action. (8 pgs).
Office Action (Notification of Reasons for Refusal) dated Aug. 12, 2014, by the Japanese Patent Office in corresponding Japanese Patent Application No. 2014-531434, and an English translation of the Office Action. (8 pgs).
Office Action (Communication Pursuant to Article 94(3) EPC) dated May 22, 2017, by the European Patent Office in corresponding European Patent Application No. 14 797 732.6 -1402. (5 pgs).
Office Action dated Feb. 11, 2017 in the corresponding Saudi Arabian Application No. 515370155, and an English translation thereof (13 pages).
Office Action dated Sep. 19, 2017 in corresponding European Patent Application No. 14 797 732.6.
English translation of the Office Action dated Jul. 25, 2017 in corresponding Thai Patent Application No. 1501006905 PCT.
English translation of the Second Substantive Examination Report dated Nov. 23, 2017 in corresponding Saudi Arabian Application No. 515370155.
Extended European Search Report dated Jun. 29, 2018 in corresponding European Patent Application No. 18176126.3.
Notification of Reasons for Refusal dated Feb. 27, 2018 in corresponding Japanese Patent Application No. 2014-236370, and an English translation thereof.
Kawano et al., "Characterization of Ca2+ Signaling Pathways in Human Mesenchymal Stem Cells," Cell Calcium, (Oct. 2002), vol. 32, No. 4, pp. 165-174.
"Mechanisms and Pharmacology of Calcium Ion Mobilization in Muscle Cells", Nihon yaskurigaku zasshi (Folia Pharmacol. japon) 94, 329-338 (1989).
Office Action issued by the Japanese Patent Office dated May 23, 2019 in corresponding Japanese Patent Application No. 2014-236370, and English language translation of Office Action (14 pages).

* cited by examiner

Fig. 1

Fig. 4

METHOD FOR PRODUCING SHEET-SHAPED CELL CULTURE

CROSS-REFERENCES TO RELATED APPLICATIONS

This application claims priority as a continuation application under 35 U.S.C. § 120 to International Application No. PCT/JP2014/063058 filed on May 16, 2014, designating the U.S., and which claims priority to Japanese Application No. 2013-105204 filed on May 17, 2013, the entire content of both of which is incorporated herein by reference.

TECHNICAL FIELD

The present disclosure generally relates to a method for producing a sheet-shaped cell culture having a high activity, a sheet-shaped cell culture produced by the production method, a pharmaceutical composition including the sheet-shaped cell culture, and a method for treating a disease using the sheet-shaped cell culture.

BACKGROUND DISCUSSION

Attempts to implant various cells have been made in order to repair damaged tissues. For example, in order to repair cardiac muscle tissues damaged by ischemic heart disease such as angina pectoris and myocardial infarction, it has been attempted to use fetal cardiac muscle cells, skeletal myoblasts, mesenchymal stem cells, cardiac stem cells, and ES cells (See, for example, Haraguchi et al., Stem Cells Transl Med. 2012 February; 1(2): 136-41).

As part of the attempts, a cell structure formed using a scaffold and a sheet-shaped cell culture, which is a sheet of cells, have been developed (See, for example, JP-T-2007-528755).

With respect to therapeutic applications of a sheet-shaped cell culture, use of a cultured epidermal sheet for skin injuries such as a burn, use of a corneal epithelial sheet-shaped cell culture for corneal injuries, and use of an oral mucosal sheet-shaped cell culture for endoscopic resection of esophageal cancer have been investigated.

In order that a sheet-shaped cell culture engrafts in the recipient tissue and carries out a desired function, it is necessary that oxygen and nutrients are supplied to the culture, and it is known that for this, effects of various cytokines such as HGF (hepatocyte growth factor) and VEGF (vascular endothelial growth factor) which have an angiogenic effect can be useful (See, for example, JP-T-2007-528755).

Therefore, the engraftment rate of a sheet-shaped cell culture and its functionality, can be improved when the cytokine productivity of the sheet-shaped cell culture are improved. In addition, it is known that these cytokines are useful for the regeneration of tissues (See, for example, Nakagami et al., J Atheroscler Thromb. 2006 April; 13(2): 77-81), and thus when the cytokines produced by a sheet-shaped cell culture act on the recipient tissue, the regeneration of the tissue can be promoted. However, no low-cost methods for improving the cytokine productivity of a sheet-shaped cell culture are known.

SUMMARY

A sheet-shaped cell culture is disclosed having a high activity such as high cytokine productivity, a production method thereof, a pharmaceutical composition containing the sheet-shaped cell culture and a method for treating a disease using the sheet-shaped cell culture.

In accordance with an exemplary embodiment, the activities of a sheet-shaped cell culture such as cytokine productivity can be improved by conducting steps of freezing and thawing cells during the production of the sheet-shaped cell culture.

A method is disclosed for producing a sheet-shaped cell culture, comprising a step of freezing cells, a step of thawing the frozen cells, and a step of forming a sheet-shaped cell culture.

According to an exemplary embodiment, the cells are autologous cells or allogeneic cells.

According to an exemplary embodiment, the cells are autologous cells.

According to an exemplary embodiment, the sheet-shaped cell culture is formed after the step of thawing the cells substantially without proliferation of the cells.

According to an exemplary embodiment, the method further comprises a step of recovering the sheet-shaped cell culture after the step of forming the sheet-shaped cell culture, wherein the step of thawing the cells is carried out within 48 hours before the step of recovering the sheet-shaped cell culture.

According to an exemplary embodiment, the method comprises a step of proliferating the cells before the step of thawing the cells.

According to an exemplary embodiment, the method comprises a step of washing the cells after the step of thawing the frozen cells and before the step of forming the sheet-shaped cell culture.

According to an exemplary embodiment, the cells are selected from the group consisting of myoblasts, mesenchymal stem cells, cardiac muscle cells, fibroblasts, cardiac stem cells, embryonic stem cells, iPS cells, synoviocytes, chondrocytes, epithelial cells, endothelial cells, hepatocytes, pancreatic cells, nephrocytes, adrenal cells, periodontal ligament cells, gingival cells, periosteal cells and skin cells.

According to an exemplary embodiment, the obtained sheet-shaped cell culture has an activity higher than the activity of a sheet-shaped cell culture produced by a method which does not comprise a step of freezing cells and a step of thawing frozen cells.

According to an exemplary embodiment, the activity is selected from the group consisting of cytokine productivity, engrafting ability, angiogenesis ability and tissue regeneration ability.

According to an exemplary embodiment, the cytokine is selected from the group consisting of HGF and VEGF.

According to an exemplary embodiment, a sheet-shaped cell culture is disclosed, which is produced by the methods as described herein.

According to an exemplary embodiment, a pharmaceutical composition is disclosed, which includes the sheet-shaped cell culture as described herein.

According to an exemplary embodiment, a method is disclosed for treating a disease associated with an abnormality of a tissue in a subject, comprising administering an effective amount of the sheet-shaped cell culture as described herein or the pharmaceutical composition as described herein to a subject in need thereof.

According to an exemplary embodiment, the tissue is selected from the group consisting of a cardiac muscle, a cornea, a retina, an esophagus, skin, a joint, cartilage, a liver, a pancreas, a gingiva, a kidney, a thyroid gland, a skeletal muscle and a middle ear.

According to an exemplary embodiment, the disease is selected from the group consisting of a cardiac disease, a corneal disease, a retinal disease, an esophageal disease, a skin disease, a joint disease, a cartilage disease, a liver disease, a pancreatic disease, a dental disease, a renal disease, a thyroid disease, a muscular disease and a middle ear disease.

Since the sheet-shaped cell culture produced by the method of the disclosure has a high activity such as high cytokine productivity and is excellent in the engraftment in a tissue, the viability and the functionality after the engraftment, the sustainability of the function, and various diseases can be treated relatively efficiently. Moreover, when the cytokines produced by the sheet-shaped cell culture produced by the method of the disclosure act on the recipient tissue, the regeneration of the tissue can be promoted. In addition, because the freezing and thawing operations in the disclosure are highly compatible with the conventional methods for producing a sheet-shaped cell culture, such that the method as disclosed can be performed relatively quickly, at a relatively low cost, and the production method of the disclosure can be used for producing a sheet-shaped cell culture.

DETAILED DESCRIPTION

Unless otherwise defined in the present description, all of the technical terms and scientific terms used in the description have the same meanings as those generally accepted by one skilled in the art. All of the patents, applications, published applications and other publications that are referred to in the description are cited in the description by reference.

In accordance with an exemplary embodiment, a method is disclosed for producing a sheet-shaped cell culture, containing a step of freezing cells, a step of thawing the frozen cells and a step of forming a sheet-shaped cell culture. In accordance with an exemplary embodiment, in the production method of the disclosure, by subjecting cells to freezing and thawing steps, cells with a low activity can be excluded while cells with a high activity remain, resulting in the improvement of the activity of the sheet-shaped cell culture as a whole.

The cells used in the production method of the disclosure are not specifically restricted as long as they can form a sheet-shaped cell culture and include adherent cells (adhesive cells) for example. Examples of the adherent cells include adherent somatic cells (such as cardiac muscle cells, fibroblasts, epithelial cells, endothelial cells, hepatocytes, pancreatic cells, nephrocytes, adrenal cells, periodontal ligament cells, gingival cells, periosteal cells, skin cells, synoviocytes and chondrocytes), tissue stem cells (such as myoblasts and cardiac stem cells), pluripotent stem cells (such as embryonic stem cells and iPS (induced pluripotent stem) cells), and mesenchymal stem cells. Accordingly, examples of the cells used in the production method of the disclosure include myoblasts (such as skeletal myoblasts), mesenchymal stem cells (such as those derived from bone marrow, adipose tissues, peripheral blood, skin, hair roots, muscle tissues, endometria, placentas and cord blood), cardiac muscle cells, fibroblasts, cardiac stem cells, embryonic stem cells, iPS cells, synoviocytes, chondrocytes, epithelial cells (such as oral mucosal epithelial cells, retinal pigment epithelial cells and nasal mucosal epithelial cells), endothelial cells (such as vascular endothelial cells), hepatocytes (such as hepatic parenchymal cells), pancreatic cells (such as pancreatic islet cells), nephrocytes, adrenal cells, periodontal ligament cells, gingival cells, periosteal cells, and skin cells.

In the disclosure, the "sheet-shaped cell culture" is a sheet formed with cells connected to each other, and can be constituted by one cell layer but also includes those constituted by two or more cell layers. The cells may be connected to each other directly (including those connected via a cellular element such as an adhesion molecule) and/or via a mediator. The mediator is not specifically restricted as long as it is a substance which can connect cells at least physically (mechanically), examples thereof can include, for example, extracellular matrix. The mediator is preferably derived from cells, for example, in particular from cells constituting the cell culture. Although the cells are connected to each other at least physically (mechanically), the cells may further be connected functionally, for example chemically or electrically.

In accordance with an exemplary embodiment, the sheet-shaped cell culture of the disclosure preferably does not contain any scaffold (support). A scaffold can be used in the present technical field in order to adhere cells on the surface thereof and/or inside thereof and maintain the physical unity of the cell culture, and a membrane of polyvinylidene difluoride (PVDF) are known for example. The cell culture of the disclosure can maintain its physical unity without the scaffold. In addition, the cell culture of the disclosure preferably consists of substances derived from the cells constituting the cell culture and does not contain any other substances.

The cells in the disclosure may be derived from living things, which can be treated with a sheet-shaped cell culture. Examples of the living things can include without restriction, human, non-human primates, dogs, cats, pigs, horses, goats, sheep, rodents (such as mice, rats, hamsters and guinea pigs), and rabbits. In addition, the cells used for forming the sheet-shaped cell culture may be of only one kind, or two or more kinds of cell may be used. In a preferable embodiment of the disclosure, when two or more kinds of cell form the cell culture, the percentage (purity) of the cells which are the highest in number is, for example, 60% or more, preferably 70% or more, more preferably 75% or more, at the time of completion of the cell culture production.

The cells may be cells derived from a different species or cells derived from the same species. Here, when the cell culture is used for implantation, the "cells derived from a different species" refer to cells derived from a living thing of a species different from the recipient species. For example, when the recipient is a human, cells derived from, for example, a monkey or a pig, are cells derived from a different species. In addition, the "cells derived from the same species" refer to cells derived from a living thing of the same species as the recipient species. For example, when the recipient is a human, human cells are cells derived from the same species. Cells derived from the same species can include self-derived cells (also referred to as self-cells or autologous cells), namely cells derived from the recipient, and cells derived from nonself of the same species (also referred to as allogeneic cells). Self-derived cells do not cause rejection when they are implanted and can be thus preferable in the disclosure. However, cells derived from a different species or cells derived from nonself of the same species can be used. When cells derived from a different species or cells derived from nonself of the same species are used, immunosuppression treatment can sometimes be necessary to inhibit the rejection. In the description, cells other than self-derived cells, namely cells derived from a different species and cells derived from nonself of the same species, can sometimes be collectively called nonself-derived cells. In an embodiment of the disclosure, the cells are autologous cells or allogeneic cells. In an embodiment of the disclosure, the cells are autologous cells. In another embodiment of the disclosure, the cells are allogeneic cells.

The step of freezing cells in the production method of the disclosure can be carried out by known methods. Examples of the method can include, without restriction, a method of subjecting cells in a container to freezing means such as a freezer, a deep freezer or a medium at a low temperature (for example, liquid nitrogen). The temperature of the freezing means is not specifically restricted as long as a part of the cell population in the container, preferably the whole cell population can be frozen, for example, the temperature can be, for example 0° C. or lower, preferably −20° C. or lower, more preferably −40° C. or lower, further preferably −80° C. or lower. The cooling rate in the freezing operation is not specifically restricted as long as the survival rate and the function of the cells after freezing and thawing are not seriously impaired, for example, the cooling rate in which cells are cooled, can be, from, for example, 4° C. to −80° C. over one to five hours, preferably over two to four hours, particularly over about three hours. In accordance with an exemplary embodiment, for example, the cells can be cooled at a rate of 0.46° C./minute. The cooling rate can be achieved by subjecting the container containing the cells to freezing means set at a desired temperature directly or with the container contained in a freezing treatment container. The freezing treatment container may have a function for controlling the rate of the temperature decrease in the container at a certain rate. As the freezing treatment container, any known containers such as BICELL® (Nihon Freezer Co., Ltd.) can be used.

The freezing operation may be conducted with the cells immersed in a culture solution, a physiological buffer or conducted after treatment of adding a cryoprotectant for protecting the cells during the freezing and thawing operations to the culture solution or replacing the culture solution with a cryopreservation solution containing a cryoprotectant. Accordingly, the production method of the disclosure may further contain a step of adding a cryoprotectant to the culture solution or a step of replacing the culture solution with a cryopreservation solution. When the culture solution is replaced with a cryopreservation solution, the cryopreservation solution may be added after substantially completely removing the culture solution or the cryopreservation solution may be added with part of the culture solution remaining, as long as a cryoprotectant is contained at an effective concentration in the solution in which the cells are immersed during freezing. Here, the "effective concentration" means a concentration at which the cryoprotectant does not exhibit toxicity but exhibits cryoprotective effects such as an effect of preventing the decrease in the survival rate, activity, function of the cells after freezing and thawing as compared with the case where the cryoprotectant is not used. The concentration can be known or can be suitably determined by a routine experiment.

The cryoprotectant used in the production method of the disclosure is not specifically restricted as long as it has a cryoprotective effect on cells, and examples thereof include dimethyl sulfoxide (DMSO), glycerol, ethylene glycol, propylene glycol, sericin, propanediol, dextran, polyvinylpyrrolidone, polyvinyl alcohol, hydroxyethyl starch, chondroitin sulfate, polyethylene glycol, formamide, acetamide, adonitol, perseitol, raffinose, lactose, trehalose, sucrose, and mannitol. One kind of cryoprotectant may be used alone, or two, three or more kinds thereof may be combined and used.

The concentration of the cryoprotectant added to the culture solution or the concentration of the cryoprotectant in the cryopreservation solution is not specifically restricted as long as the concentration is the effective concentration defined above but can be, for example, from 2 to 20% (v/v) relative to the total of the culture solution or the cryopreservation solution for example. However, an alternative use concentration, which is outside the concentration range but is known for a certain cryoprotectant or is experimentally determined, can also be used, and such a concentration is also included in the scope of the disclosure.

The step of thawing the frozen cells in the production method of the disclosure can be carried out by known methods for thawing cells, for example, the step can be achieved by subjecting the frozen cells to thawing means such as a solid, liquid or gas medium (for example, water) at a temperature higher than the freezing temperature, a water bath, an incubator or a thermostat or by immersing the frozen cells in a medium (for example, a culture solution) at a temperature higher than the freezing temperature, although the step is not restricted to these methods. The temperature of the thawing means or the immersion medium is not specifically restricted as long as it is a temperature at which the cells can be thawed within a desired time but can be, for example, from 4° C. to 50° C., preferably from 30° C. to 40° C., more preferably from 36° C. to 38° C. Also, the thawing period is not specifically restricted as long as the survival rate and the function of the thawed cells are not seriously impaired but can be, for example, two minutes or shorter, and in particular, the decrease in the survival rate can be prevented significantly when the thawing period is, for example, 20 seconds or shorter. In accordance with an exemplary embodiment, the thawing period can be controlled by adjusting the temperature of the thawing means or the immersion medium, the volume or the composition of the culture solution or the cryopreservation solution for freezing.

The production method of the disclosure may contain a step of washing the cells after the step of thawing the frozen cells and before the step of forming the sheet-shaped cell culture. The cells can be washed by known methods and can include, for example, suspending the cells in a liquid (such as a culture solution or a physiological buffer containing or not containing serum or a serum component (serum albumin)), centrifuging the suspension, discarding the supernatant and recovering the precipitated cells, although the step is not restricted to this example. In the step of washing the cells, the cycle of suspending, centrifugation and recovery may be conducted once or more than once (for example, two, three, four, or five times). In an exemplary embodiment of the disclosure, the step of washing the cells can be carried out immediately after the step of thawing the frozen cells.

The step of forming a sheet-shaped cell culture in the production method of the disclosure can be carried out by known methods. Examples of the method can include, without restriction, the method described in JP-T-2007-528755. The step of forming a sheet-shaped cell culture may contain a step of seeding cells on a culture substrate and a step of forming a sheet with the seeded cells.

The culture substrate is not specifically restricted as long as cells can form a cell culture on the culture substrate, and examples can include containers made of various materials, a solid or semisolid surface in a container. The structure and material of the container preferably do not allow permeation of a liquid such as a culture solution. Examples of the material can include, without restriction, polyethylene, polypropylene, Teflon (registered trademark), polyethylene terephthalate, polymethyl methacrylate, nylon 6,6, polyvinyl alcohol, cellulose, silicon, polystyrene, glass, polyacrylamide, polydimethylacrylamide, and metals (such as iron, stainless, aluminum, copper and brass). The container preferably has at least one flat surface. Examples of the container can include, without restriction, a cell culture dish, and a cell culture bottle. In addition, the container may have a solid or semisolid surface in its inside. Examples of the solid surface can include a plate, a container and the like made of the various materials above, and examples of the semisolid surface include a gel, and a soft polymer matrix. The culture substrate may be produced using the materials, or a commercially available culture substrate may be used. Examples of a preferable culture substrate can include, without restriction, a substrate having an adhesive surface suitable for the formation of a sheet-shaped cell culture. In accordance with an exemplary embodiment, examples of the culture substrate can include a substrate having a hydrophilic surface, for example, a substrate with a surface coated with a hydrophilic compound such as polystyrene, collagen gel and a hydrophilic polymer which has been subjected to corona discharge treatment; a substrate with a surface coated with extracellular matrix such as collagen, fibronectin, laminin, vitronectin, proteoglycan and glycosaminoglycan, a cell adhesion molecule such as those of cadherin family, and selectin family and integrin family. Such a substrate is commercially available (for example, Corning® TC-Treated Culture Dish).

The surface of the culture substrate may be covered with a material whose physical properties change in response to a stimulus such as temperature or light. As the material, without restriction, for example, known materials such as the following materials can be used a temperature-responsive material made of a homopolymer or a copolymer of a (meth)acrylamide compound, an N-alkyl-substituted (meth)acrylamide derivative (such as N-ethylacrylamide, N-n-propylacrylamide, N-n-propylmethacrylamide, N-isopropylacrylamide, N-isopropylmethacrylamide, N-cyclopropylacrylamide, N-cyclopropylmethacrylamide, N-ethoxyethylacrylamide, N-ethoxyethylmethacrylamide, N-tetrahydrofurfurylacrylamide and N-tetrahydrofurfurylmethacrylamide), an N,N-dialkyl-substituted (meth)acrylamide derivative (such as N,N-dimethyl(meth)acrylamide, N,N-ethylmethylacrylamide and N,N-diethylacrylamide), a (meth)acrylamide derivative having a cyclic group (such as 1-(1-oxo-2-propenyl)-pyrrolidine, 1-(1-oxo-2-propenyl)-piperidine, 4-(1-oxo-2-propenyl)-morpholine, 1-(1-oxo-2-methyl-2-propenyl)-pyrrolidine, 1-(1-oxo-2-methyl-2-propenyl)-piperidine and 4-(1-oxo-2-methyl-2-propenyl)-morpholine) or a vinyl ether derivative (such as methyl vinyl ether); a light-absorbing polymer having an azobenzene group; a light-responsive material such as a copolymer of a vinyl derivative of triphenylmethane leuco hydroxide and an acrylamide-based monomer and N-isopropylacrylamide gel containing spirobenzopyran (see for example JP-A-2-211865 and JP-A-2003-33177). By applying a certain stimulus to these materials, the physical properties such as hydrophilicity and hydrophobicity can be changed, and the peeling of a cell culture adhered to the materials can be promoted. Culture dishes covered with a temperature-responsive material are commercially available (for example, UpCell® of CellSeed Inc.), and the culture dishes can be used for the production method of the disclosure.

The culture substrate may have any shape but is preferably flat. The area thereof is not specifically restricted but can be, for example, from 1 to 200 $cm^2$, preferably from 2 to 100 $cm^2$, more preferably from 3 to 50 $cm^2$.

In accordance with an exemplary embodiment, the culture substrate may be coated (covered or coated) with serum. When a culture substrate coated with serum is used, a sheet-shaped cell culture with a higher density can be formed. The term "coated with serum" means the state in which a serum component is adhered to the surface of the culture substrate. The state can be achieved, for example, by treating the culture substrate with serum, without restriction. The treatment with serum can include bringing serum into contact with the culture substrate and if necessary, incubating for a certain period of time. As the serum, serum of a different species and serum of the same species can be used. When the cell culture is used for implantation, the serum of a different species refers to serum derived from a living thing of a species different from the recipient species. For example, when the recipient is a human, bovine or horse serum such as fetal bovine/calf serum (FBS or FCS), calf serum (CS) and horse serum (HS) is serum of a different species. The "serum of the same species" refers to serum derived from a living thing of the same species as the recipient species. For example, when the recipient is a human, human serum is serum of the same species. Serum of the same species can include self-serum (also called autologous serum), which is serum derived from the recipient, and allogeneic serum, which is derived from an individual which is of the same species but is not the recipient. In the description, serum other than self-serum, namely serum of a different species and allogeneic serum are sometimes collectively referred to as nonself-serum.

Serum used for coating the culture substrate is either commercially available or can be prepared from blood collected from a desired living thing by a conventional method. In accordance with an exemplary embodiment, for example, a method in which collected blood is coagulated by leaving the blood at room temperature for, for example, about 20 to 60 minutes and centrifuged at around, for example, 1000 to 1200×g and the supernatant is collected.

When serum is incubated on the culture substrate, an undiluted serum solution may be used, or a diluted serum solution may be used. The serum can be diluted using any medium such as water, physiological saline, various buffers (for example, PBS, and HBS) and various liquid media (for example, DMEM, MEM, F12, DME, RPMI1640, MCDB (MCDB102, 104, 107, 120, 131, 153, and 199), L15, SkBM, RITC80-7, and DMEM/F12) without restriction. The dilution ratio is not specifically restricted as long as the serum component can adhere to the culture substrate and is from 0.5 to 100% (v/v) for example, preferably from 1 to 60% (v/v), more preferably from 5 to 40% (v/v).

The incubation period is not specifically restricted, either, as long as the serum component can adhere to the culture substrate and is from 1 to 72 hours for example, preferably from 4 to 48 hours, more preferably from 5 to 24 hours, further preferably from 6 to 12 hours. The incubation temperature is not specifically restricted, either, as long as the serum component can adhere to the culture substrate and is from, for example, 0 to 60° C. for example, preferably from 4 to 45° C., more preferably from room temperature to 40° C.

The serum may be discarded after the incubation. As the method for discarding the serum, general methods for discarding a liquid such as suction with a pipette and decantation can be used. In a preferable embodiment of the disclosure, the culture substrate may be washed with a serum-free washing solution after discarding the serum. The serum-free washing solution is not specifically restricted as long as it is a liquid medium which does not contain serum and which does not adversely affect the serum component adhered to the culture substrate, and include any medium such as water, physiological saline, various buffers (for example, PBS and HBS) and various liquid media (for example, DMEM, MEM, F12, DME, RPMI1640, MCDB (MCDB102, 104, 107, 120, 131, 153, and 199), L15, SkBM, RITC80-7, and DMEM/F12) without restriction. As the washing method, general methods for washing a culture substrate such as a method in which a serum-free washing solution is added to the culture substrate, stirred for a certain period of time (for example, 5 to 60 seconds) and then discarded can be used without restriction.

In the disclosure, the culture substrate may be coated with a growth factor. The "growth factor" here means a substance, which promotes the proliferation of cells as compared to the case without the substance, and examples thereof can include epithelial growth factors (EGFs), vascular endothelial growth factors (VEGFs), and fibroblast growth factors (FGFs). The method for coating the culture substrate with a growth factor, the discarding method and the washing method are basically same as those for serum except that the dilution ratio during the incubation is from 0.0001 µg/mL to 1 µg/mL for example, preferably from 0.0005 µg/mL to 0.05 µg/mL, more preferably from 0.001 µg/mL to 0.01 µg/mL.

In the disclosure, the culture substrate may be coated with a steroid. The "steroid" here means a compound having a steroid nucleus, which may have adverse effects such as adrenocortical insufficiency and Cushing's syndrome on a living body. Examples of the compound include, without restriction, cortisol, prednisolone, triamcinolone, dexamethasone, and betamethasone. The method for coating the culture substrate with a steroid, the discarding method and the washing method are basically same as those for serum except that the dilution ratio during the incubation is, in terms of dexamethasone, from 0.1 µg/mL to 100 µg/mL for example, preferably from 0.4 µg/mL to 40 µg/mL, more preferably from 1 µg/mL to 10 µg/mL.

The culture substrate may be coated with any one of serum, a growth factor and a steroid or may be coated with any combination thereof, namely combination of serum and a growth factor, of serum and a steroid, of serum, a growth factor and a steroid or of a growth factor and a steroid. When the culture substrate is coated with more than one component, the culture substrate may be coated simultaneously with a mixture of the components or coated in separate steps.

Cells may be seeded to the culture substrate immediately after coating the culture substrate with serum, or the culture substrate may be stored after coating and then cells may be seeded. A coated substrate can be stored for a long time by keeping it for example at 4° C. or lower, preferably −20° C. or lower, more preferably −80° C. or lower.

Cells can be seeded to the culture substrate by known methods and under known conditions. Cells may be seeded to the culture substrate, for example, by pouring a cell suspension prepared by suspending cells in a culture solution into the culture substrate (culture container). An instrument suitable for the operation of pouring the cell suspension such as a dropper and a pipette can be used for pouring the cell suspension.

In a preferable exemplary embodiment of the disclosure, cells are seeded at a density at which the cells can form a sheet-shaped cell culture substantially without proliferation. The "density at which the cells can form a sheet-shaped cell culture substantially without proliferation" means a cell density at which a sheet-shaped cell culture can be formed when the cells are cultured in a non-proliferating culture solution, which contains substantially no growth factor. For example, in the case of skeletal myoblasts, cells are seeded to a culture substrate at a density of about 6,500 cells/cm$^2$ to form a sheet-shaped cell culture in a method using a culture solution containing a growth factor (for example, see JP-T-2007-528755), but a sheet-shaped cell culture is not formed when cells at the density are cultured in a culture solution containing no growth factor. Accordingly, the seeding density in the embodiment is higher than the density in a method using a culture solution containing a growth factor. In accordance with an exemplary embodiment, the density can be $1.0 \times 10^5$ cells/cm$^2$ or more for skeletal myoblasts for example. The upper limit of the seeding density is not specifically restricted as long as the formation of the cell culture is not prevented and the cells do not undergo the transition to the differentiation but is less than, for example, $3.4 \times 10^6$ cells/cm$^2$ for skeletal myoblasts.

Accordingly, the "density at which the cells can form a sheet-shaped cell culture substantially without proliferation" for skeletal myoblasts is from, for example, $1.0 \times 10^5$ to $3.4 \times 10^6$ cells/cm$^2$ in an embodiment, from $3.0 \times 10^5$ to $3.4 \times 10^6$ cells/cm$^2$ in another embodiment, from $3.5 \times 10^5$ to $3.4 \times 10^6$ cells/cm$^2$ in still another embodiment, from $1.0 \times 10^6$ to $3.4 \times 10^6$ cells/cm$^2$ in still another embodiment, from $3.0 \times 10^5$ to $1.7 \times 10^6$ cells/cm$^2$ in still another embodiment, from $3.5 \times 10^5$ to $1.7 \times 10^6$ cells/cm$^2$ in another embodiment, and from $1.0 \times 10^6$ to $1.7 \times 10^6$ cells/cm$^2$ in further another embodiment. Each of the above ranges may include both of the upper limit and the lower limit or one of the upper limit and the lower limit, as long as the upper limit is less than $3.4 \times 10^6$ cells/cm$^2$. Accordingly, the density may be for example $3.0 \times 10^5$ cells/cm$^2$ or more and less than $3.4 \times 10^6$ cells/cm$^2$ (including the lower limit but not including the upper limit), $3.5 \times 10^5$ cells/cm$^2$ or more and less than $3.4 \times 10^6$ cells/cm$^2$ (including the lower limit but not including the upper limit), $1.0 \times 10^6$ cells/cm$^2$ or more and less than $3.4 \times 10^6$ cells/cm$^2$ (including the lower limit but not including the upper limit), more than $1.0 \times 10^6$ cells/cm$^2$ and less than $3.4 \times 10^6$ cells/cm$^2$ (including neither the lower limit nor the upper limit) or more than $1.0 \times 10^6$ cells/cm$^2$ and $1.7 \times 10^6$ cells/cm$^2$ or less (not including the lower limit but including the upper limit). One skilled in the art can suitably determine the cell density suitable for the disclosure with respect to cells other than skeletal myoblasts by an experiment according to the disclosure of the description.

The step of forming a sheet with the seeded cells can also be carried out by known methods and under known conditions. Unrestricted examples of the method are described, for example in JP-T-2007-528755. In accordance with an exemplary embodiment, a sheet-formation of cells can be achieved by the adhesion of cells by the intercellular adhesion mechanism such as an adhesion molecule and extracellular matrix. Accordingly, the step of forming a sheet with the seeded cells can be achieved, for example, by culturing the cells under a condition under which intercellular adhesion is caused. The condition may be any condition as long as intercellular adhesion can be caused but in general, intercellular adhesion can be caused under a condition similar to the general cell cultivation condition. The condition can be, for example, cultivation at 37° C. in 5% $CO_2$. In addition, the cultivation can be carried out at normal pressure (atmospheric pressure). One skilled in the art can select the optimum condition depending on the kind of seeded cells. In the description, the cultivation for forming a sheet with the seeded cells is sometimes called "sheet-formation cultivation".

In an exemplary embodiment of the disclosure, the cultivation of cells can be carried out within a certain period, preferably within a period in which the cells do not undergo the transition to the differentiation. Therefore, in the exemplary embodiment, the cells can be maintained in the undifferentiated state over the cultivation period. The transition of cells to the differentiation can be evaluated by methods known to one skilled in the art. For example, in the case of skeletal myoblasts, the expression of MHC, the creatine kinase (CK) activity, the multinucleation of cells, the myotube formation can be used as indicators of differentiation. In a preferable embodiment of the disclosure, the cultivation period is, for example, within 48 hours, more preferably within 40 hours, further preferably within 24 hours.

The cell culture solution used for the cultivation (sometimes simply referred to as "culture solution" or "culture medium") is not specifically restricted as long as the cells can be kept alive, but, for example, a cell culture solution containing an amino acid, a vitamin and an electrolyte as main components can be used. In an embodiment of the disclosure, the culture solution contains a basal medium for cell cultivation as a base. The basal medium can include DMEM, MEM, F12, DME, RPMI1640, MCDB (MCDB102, 104, 107, 120, 131, 153, and 199), L15, SkBM, RITC80-7, and DMEM/F12) without restriction. Many of the basal media are commercially available, and their compositions have been disclosed.

The basal medium may be used with the standard composition (for example, in the commercially distributed state), or its composition may be suitably changed in accordance with the cell kind or the cell condition. Accordingly, the basal medium used in the disclosure is not restricted to those having known compositions and includes those in which one or two or more components are added, removed, increased in amount or decreased in amount.

Examples of the amino acid contained in the basal medium can include, without restriction, L-arginine, L-cystine, L-glutamine, glycine, L-histidine, L-isoleucine, L-leucine, L-lysine, L-methionine, L-phenylalanine, L-serine, L-threonine, L-tryptophan, L-tyrosine, and L-valine. Examples of the vitamin can include, without restriction, calcium D-pantothenate, choline chloride, folic acid, i-inositol, niacinamide, riboflavin, thiamine, pyridoxine, biotin, lipoic acid, vitamin B12, adenine, and thymidine. Examples of the electrolyte can include, without restriction, $CaCl_2$, KCl, $MgSO_4$, NaCl, $NaH_2PO_4$, $NaHCO_3$, $Fe(NO_3)_3$, $FeSO_4$, $CuSO_4$, $MnSO_4$, $Na_2SiO_3$, $(NH_4)_6Mo_7O_{24}$, $NaVO_3$, $NiCl_2$, and $ZnSO_4$. In addition to these components, the basal medium may contain a saccharide such as D-glucose, sodium pyruvate, a pH indicator such as phenol red, and putrescine.

In an exemplary embodiment of the disclosure, the concentrations of the amino acids contained in the basal medium can be, for example, 63.2 to 84 mg/L L-arginine, 35 to 63 mg/L L-cystine, 4.4 to 584 mg/L L-glutamine, 2.3 to 30 mg/L glycine, 42 mg/L L-histidine, 66 to 105 mg/L L-isoleucine, 105 to 131 mg/L L-leucine, 146 to 182 mg/L L-lysine, 15 to 30 mg/L L-methionine, 33 to 66 mg/L L-phenylalanine, 32 to 42 mg/L L-serine, 12 to 95 mg/L L-threonine, 4.1 to 16 mg/L L-tryptophan, 18.1 to 104 mg/L L-tyrosine and 94 to 117 mg/L L-valine.

In an exemplary embodiment of the disclosure, the concentrations of the vitamins contained in the basal medium can be, for example, 4 to 12 mg/L calcium D-pantothenate, 4 to 14 mg/L choline chloride, 0.6 to 4 mg/L folic acid, 7.2 mg/L inositol, 4 to 6.1 mg/L niacinamide, 0.0038 to 0.4 mg/L riboflavin, 3.4 to 4 mg/L thiamine and 2.1 to 4 mg/L pyridoxine.

The cell culture solution may contain one or two or more kinds of additive such as serum, a growth factor, a steroid component and a selenium component, in addition to the above components. However, these components are impurities introduced during the production steps and may cause side effects such as anaphylactic shock on the recipient in clinical practice, and it can be desirable to exclude these components in the application to a clinical use. Accordingly, in a preferable embodiment of the disclosure, the cell culture solution does not contain an effective amount of at least one kind of these additives. In a more preferable exemplary embodiment of the disclosure, the cell culture solution does not substantially contain at least one kind of these additives. Moreover, in a particularly preferable exemplary embodiment of the disclosure, the cell culture solution contains substantially no additive. Therefore, the cell culture solution may contain a basal medium only.

In an exemplary embodiment of the disclosure, the cell culture solution contains substantially no serum. In the description, a cell culture solution that contains substantially no serum is sometimes referred to as a "serum-free culture medium". Here, the expression "contains substantially no serum" means that the serum content in the culture solution is at a level which does not cause any adverse effect when the cell culture is applied to a living body (for example, an amount at which the serum albumin content in the cell culture is less than 50 ng) and preferably means that these substances are not actively added to the culture solution. In the disclosure, in order to prevent a side effect of the implantation, the cell culture solution preferably contains substantially no serum of a different species and further preferably contains substantially no nonself-serum.

In an exemplary embodiment of the disclosure, the cell culture solution does not contain an effective amount of a growth factor. Here, "an effective amount of a growth factor" means an amount of a growth factor, which promotes the proliferation of cells with significance as compared to the case without the growth factor or for convenience an amount which is generally added for the purpose of proliferating cells in the technical field. The significance of promotion of the cell proliferation can be suitably evaluated for example by any statistical method known in the technical field such as t test, and the generally added amount can be known from various publications in the technical field. In accordance with an exemplary embodiment, the effective amount of EGF for the cultivation of skeletal myoblasts can be, for example, 0.005 μg/mL or more.

Accordingly, the expression "does not contain an effective amount of a growth factor" means that the concentration of the growth factor in the culture solution in the disclosure is lower than the effective amount. For example, the concentration of EGF in the culture solution for the cultivation of skeletal myoblasts can be, for example, preferably less than 0.005 μg/mL, more preferably less than 0.001 μg/mL. In a preferable exemplary embodiment of the disclosure, the concentration of a growth factor in the culture solution is lower than the general concentration in a living body. In the embodiment, for example, the concentration of EGF in the culture solution for the cultivation of skeletal myoblasts can be, for example, preferably less than 5.5 ng/mL, more preferably less than 1.3 ng/mL, further preferably less than 0.5 ng/mL. In a further preferable exemplary embodiment, the culture solution in the disclosure contains substantially no growth factor. Here, that the culture solution contains substantially no growth factor means that the growth factor content in the culture solution is at a level, which does not cause any adverse effect when the cell culture is applied to a living body and preferably means that a growth factor is not actively added to the culture solution. Accordingly, in the embodiment, the culture solution does not contain a growth factor in a concentration same as or more than the concentration contained in the other components such as serum.

In an exemplary embodiment of the disclosure, the cell culture solution contains substantially no steroid component. Here, the "steroid component" means, among compounds having a steroid nucleus, a compound, which may have adverse effects such as adrenocortical insufficiency and Cushing's syndrome on a living body. Examples of the compound include, without restriction, cortisol, prednisolone, triamcinolone, dexamethasone, and betamethasone. Accordingly, the expression "contains substantially no steroid component" means that the content of the compounds in the culture solution is at a level which does not cause any adverse effect when the cell culture is applied to a living body and preferably means that the compounds are not actively added to the culture solution, which means that the culture solution does not contain any steroid component in a concentration same as or more than the concentration contained in the other components such as serum.

In an exemplary embodiment of the disclosure, the cell culture solution contains substantially no selenium component. Here, the "selenium component" can include a selenium molecule and a selenium-containing compound, for example, a selenium-containing compound capable of releasing a selenium molecule in a living body, such as selenous acid. Accordingly, the expression "contains substantially no selenium component" means that the content of the substances in the culture solution is at a level which does not cause any adverse effect when the cell culture is applied to a living body and preferably means that the substances are not actively added to the culture solution, which means that the culture solution does not contain any selenium component in a concentration same as or more than the concentration contained in the other components such as serum. In accordance with an exemplary embodiment, for example, in the case of human, the selenium concentration in the culture solution is lower than a value derived by multiplying the normal value in human serum (for example, 10.6 to 17.4 μg/dL) by the ratio of human serum contained in the culture medium (that is, when the human serum content is 10%, the selenium concentration is less than 1.0 to 1.7 μg/dL for example).

In the preferable exemplary embodiment of the disclosure, a step of removing impurities introduced during the production steps such as a growth factor, a steroid component and a serum component of a different species by washing, which has been necessary for producing a cell culture to be applied to a living body, is not necessary. Accordingly, an embodiment of the method of the disclosure does not contain a step of removing the impurities introduced during the production steps.

Here, the "impurities introduced during the production steps" can include the following substances introduced in the respective production steps. For example, the impurities can be those derived from the cell substrate (for example, proteins derived from the host cells and DNA derived from the host cells), those derived from the cell culture solution (for example, inducers, antibiotics and medium components), those introduced during the steps of extracting, separating, processing and purifying the target substance, which are conducted after the cell cultivation (for example, see Notification No. 571 issued by Pharmaceutical and Food Safety Bureau).

The cultivation of cells can be carried out under a condition which is generally employed in the technical field. For example, a cultivation condition can be cultivation at 37° C. in 5% $CO_2$. In addition, the cultivation can be carried out at normal pressure (atmospheric pressure). From the viewpoints of sufficiently forming a cell culture and of preventing the cell differentiation, the cultivation period is, for example, preferably within 48 hours, more preferably within 40 hours, further preferably within 24 hours. The cultivation can be carried out in a container of any size and shape. The size and shape of a cell culture can be adjusted by adjusting the size/shape of the cell-adhesion surface of the culture container or by providing a form with desired size/shape on the cell-adhesion surface of the culture container and culturing the cells in the form.

In an exemplary embodiment of the production method of the disclosure, the sheet-shaped cell culture is formed after the step of thawing the cells substantially without proliferation of the cells. This procedure can further increase the activity of the sheet-shaped cell culture.

The expression "substantially without proliferation" of the cells means that the cells are not proliferated to an extent going beyond the measurement error, and whether the cells have proliferated or not can be evaluated for example by comparing the number of seeded cells and the number of cells after forming the cell culture. In the disclosure, the number of cells after forming the sheet-shaped cell culture can be, for example, 300% or less, preferably 200% or less, more preferably 150% or less, further preferably 125% or less, particularly preferably 100% or less based on the number of seeded cells.

Because the proliferation of cells depends on various conditions such as the number of seeded cells (density of seeded cells), the cultivation environment (for example, cultivation period, and cultivation temperature) and the composition of the culture medium, the cells cannot be substantially proliferated by adjusting the conditions. Among the conditions, by increasing the density of seeded cells, the sheet-shaped cell culture can be obtained in a relatively short time while the proliferation of the cells can be prevented, and thus it can be preferable in the disclosure to control the proliferation with the density of seeded cells. The density at which the sheet-shaped cell culture can be formed substantially without proliferation of the cells has already been described above.

Accordingly, in the exemplary embodiment, the sheet-formation cultivation can be carried out after the step of thawing the cells without any further step of proliferating the cells, under a condition under which the cells are not substantially proliferated. In addition, in the embodiment, a step which does not involve cell proliferation such as a step of washing the cells can be carried out after the step of thawing the cells and before the sheet-formation cultivation.

The production method of the disclosure may further contain a step of recovering the formed sheet-shaped cell culture after the step of forming the sheet-shaped cell culture. The recovery of the sheet-shaped cell culture is not specifically restricted as long as the sheet-shaped cell culture can be released (peeled) from the culture substrate as the scaffold while keeping its sheet structure at least partially, and for example, the sheet-shaped cell culture can be recovered by enzyme treatment using a protease (for example, trypsin) and/or by mechanical treatment such as pipetting. In addition, when the cells are cultured on a culture substrate with a surface covered with a material whose physical properties change in response to a stimulus such as temperature or light and the cell culture is thus formed, the sheet-shaped cell culture can be released nonenzymatically by applying a certain stimulus.

An exemplary embodiment of the production method of the disclosure further contains a step of recovering the sheet-shaped cell culture after the step of forming the sheet-shaped cell culture, and the step of thawing the cells is carried out within 48 hours before the step of recovering the sheet-shaped cell culture. By controlling the interval between the step of thawing the cells and the step of recovering the sheet-shaped cell culture to be, for example, 48 hours or shorter, preferably 36 hours or shorter, more preferably 24 hours or shorter, the activity of the sheet-shaped cell culture can be further increased.

The production method of the disclosure may further contain a step of proliferating the cells before the step of thawing the cells. The step of proliferating the cells may be carried out by known methods, and one familiar with the cultivation conditions suitable for the proliferation of respective cell kinds. In the production method of the disclosure, when the sheet-shaped cell culture is formed after the step of thawing the cells substantially without proliferation of the cells or when the step of thawing the cells is carried out within, for example, 48 hours before the step of recovering the sheet-shaped cell culture, it can be useful to carry out the step of proliferating the cells before the step of thawing the cells in order to obtain a desired number of cells.

In an exemplary embodiment, the production method of the disclosure does not contain a step of introducing a gene into the cells. In another exemplary embodiment, the production method of the disclosure contains a step of introducing a gene into the cells. The gene to be introduced is not specifically restricted as long as it is useful for treating the target disease, and the gene may be a cytokine such as HGF and VEGF for example. The gene can be introduced by known methods such as calcium phosphate transfection, lipofection, ultrasonic transfection, electroporation, particle gun method, a method using a virus vector such as an adenovirus vector or a retrovirus vector and microinjection. The gene can be introduced into the cells for example before the step of thawing the cells without restriction.

The sheet-shaped cell culture obtained by the production method of the disclosure has an activity higher than that of a sheet-shaped cell culture produced by the same method as the production method of the disclosure except that the method does not contain a step of freezing the cells and a step of thawing the frozen cells (hereinafter, sometimes referred to as the control sheet-shaped cell culture). Examples of the activity can include, without restriction, cytokine productivity, engrafting ability, angiogenesis ability, and tissue regeneration ability. Here, that the activity is higher means that the activity is higher than the activity of the control sheet-shaped cell culture, without restriction, for example by 5% or more, 10% or more, 20% or more, 30% or more, 40% or more, 50% or more, 60% or more, 70% or more, 80% or more, 90% or more or 100% or more.

In the disclosure, the cytokine means a proteinaceous factor which is released from a cell and mediates various intercellular interactions. Accordingly, the cytokine in the disclosure is not restricted to those released from immune cells. In an exemplary embodiment of the disclosure, the cytokine is useful for the engraftment of the sheet-shaped cell culture in the recipient tissue. In an exemplary embodiment of the disclosure, the cytokine is useful for the angiogenesis. In an exemplary embodiment of the disclosure, the cytokine is useful for the regeneration of a tissue. Such a cytokine is known in the technical field, and one skilled in the art can determine an appropriate cytokine based on known information. In an embodiment of the disclosure, the cytokine can include a growth factor. In an exemplary embodiment of the disclosure, the cytokine is selected from the group consisting of HGF and VEGF. Accordingly, in an exemplary embodiment of the disclosure, the cytokine productivity is the growth factor productivity. In addition, in an exemplary embodiment of the disclosure, the cytokine productivity is the productivity of a growth factor selected from the group consisting of HGF and VEGF.

The activity of the sheet-shaped cell culture can be quantified by various methods. When the activity is cytokine productivity, for example, the cytokine productivity can be quantified by culturing the sheet-shaped cell culture in a culture solution for a certain period of time and measuring the amount of a cytokine secreted into the culture solution or measuring the amount of a cytokine gene expressed in the sheet-shaped cell culture. Methods for measuring the amount of a certain protein or the level of gene expression are known in the technical field. Examples of the method for measuring the amount of a protein include, without restriction, electrophoresis, Western blotting, mass spectrometry, EIA, ELISA, RIA, immunohistochemical method, and immunocytochemical method; and examples of the method for measuring the level of gene expression include, without restriction, Northern blotting, Southern blotting, DNA microarray analysis, RNase protection assay, PCR methods such as RT-PCR and real-time PCR, and in situ hybridization.

When the activity is engrafting ability, the engrafting ability can be quantified by applying the sheet-shaped cell culture to a tissue, observing the state of the applied sheet-shaped cell culture, for example, the adhesion to the tissue, the size, color and form of the remaining culture, after a certain period of time and giving scores to them. When the activity is angiogenesis ability, the angiogenesis ability can be quantified by applying the sheet-shaped cell culture to a tissue, observing the states of the applied sheet-shaped cell culture and the part of the tissue to which the sheet-shaped cell culture was applied, for example the presence or absence of angiogenesis, after a certain period of time and giving scores to the states. When the activity is tissue regeneration ability, the tissue regeneration ability can be quantified by applying the sheet-shaped cell culture to a tissue, observing the state of the part of the tissue to which the sheet-shaped cell culture was applied (recipient), for example, the tissue size, the microstructure of the tissue, the ratios of the damaged tissue and the normal tissue, and the function of the tissue, after a certain period of time and giving scores to them.

In an exemplary embodiment, all of the steps of the production method of the disclosure can be carried out in vitro. In another exemplary embodiment, the production method of the disclosure contains a step carried out in vivo, for example, without restriction, a step of collecting cells or a tissue serving as a source of cells from the subject. In an exemplary embodiment, all of the steps of the production method of the disclosure can be carried out under a sterile condition. In an embodiment, the production method of the disclosure can be carried out in such a manner that the sheet-shaped cell culture obtained in the end becomes substantially sterile. In an exemplary embodiment, the production method of the disclosure can be carried out in such a manner that the sheet-shaped cell culture obtained in the end becomes sterile.

Another aspect of the disclosure relates to a sheet-shaped cell culture produced by the production method of the disclosure. The sheet-shaped cell culture of the disclosure can be characterized by having an activity higher than that of the control sheet-shaped cell culture. Details of the degree of the high activity are as described above. In an embodiment, an activity of the sheet-shaped cell culture of the disclosure selected from the group consisting of cytokine productivity, engrafting ability, angiogenesis ability and tissue regeneration ability is higher than that of the control sheet-shaped cell culture. In addition, in an exemplary embodiment, the productivity of a cytokine selected from the group consisting of HGF and VEGF of the sheet-shaped cell culture of the disclosure is higher than that of the control sheet-shaped cell culture. Because the sheet-shaped cell culture of the disclosure has a higher activity, it can exhibit better effects than the control sheet-shaped cell culture in various therapeutic applications. For example, when the HGF and/or VEGF productivity is high, engraftment in the tissue, angiogenesis and tissue regeneration are promoted, and the sheet-shaped cell culture functions continuously over a long period, resulting in the enhancement of the therapeutic effects.

The sheet-shaped cell culture of the disclosure can be useful for treating various diseases associated with abnormalities of tissues. Accordingly, in an embodiment, the sheet-shaped cell culture of the disclosure is for use in treating a disease associated with an abnormality of a tissue. Because the sheet-shaped cell culture of the disclosure has properties inherent in the constituent cells which are similar to those of a conventional sheet-shaped cell culture except that it has a higher activity, the sheet-shaped cell culture of the disclosure can be applied at least to a tissue or a disease which can be treated with a conventional sheet-shaped cell culture. Examples of the tissue to be treated can include, without restriction, a cardiac muscle, a cornea, a retina, an esophagus, skin, a joint, cartilage, a liver, a pancreas, a gingiva, a kidney, a thyroid gland, a skeletal muscle, and a middle ear. In addition, examples of the disease to be treated can include, without restriction, cardiac diseases (for example, myocardiopathy (myocardial infarction and cardiac injury), and cardiomyopathy), corneal diseases (for example, corneal epithelial stem cell deficiency, corneal injury (thermal/chemical corrosion), corneal ulcer, corneal opacity, corneal perforation, corneal scar, Stevens-Johnson syndrome, and ocular pemphigoid), retinal diseases (for example, retinitis pigmentosa, and age-related macular degeneration), esophageal diseases (for example, prevention of esophageal inflammation/stricture after esophageal surgery (removal of esophageal cancer)), skin diseases (for example, skin injury (external injury and burn)), joint diseases (for example, and osteoarthritis), cartilage diseases (for example, cartilage damage), liver diseases (for example, chronic liver disease), pancreatic diseases (for example, diabetes), dental diseases (for example, periodontal disease), renal diseases (for example, renal failure, renal anemia, and renal osteodystrophy), thyroid diseases (for example, and hypothyroidism), muscular diseases (for example, muscle damage and muscle inflammation) and middle ear diseases (for example, otitis media).

The disclosure that the sheet-shaped cell culture is effective against the above diseases is described, for example in JP-T-2007-528755, Haraguchi et al., Stem Cells Transl Med. 2012 February; 1(2): 136-41, Arauchi et al., Tissue Eng Part A. 2009 December; 15(12):3943-9; Ito et al., Tissue Eng. 2005 March-April; 11(3-4):489-96; Yaji et al., Biomaterials. 2009 February; 30(5):797-803; Yaguchi et al., Acta Otolaryngol. 2007 October; 127(10):1038-44; Watanabe et al., Transplantation. 2011 April 15; 91(7):700-6; Shimizu et al., Biomaterials. 2009 October; 30(30):5943-9; Ebihara et al., Biomaterials. 2012 May; 33(15):3846-51; and Takagi et al., World J Gastroenterol. 2012 October 7; 18(37):5145-50.

The sheet-shaped cell culture of the disclosure can be applied to the tissue to be treated and used for repairing or regenerating the tissue, but the sheet-shaped cell culture can also be implanted to a part other than the tissue to be treated (for example, subcutaneous tissues) as a source of a bioactive substance such as a hormone (for example, Arauchi et al., Tissue Eng Part A. 2009 December; 15(12):3943-9, Shimizu et al., Biomaterials. 2009 October; 30(30):5943-9). Also, by fragmenting the sheet-shaped cell culture into a size which can be administered by injection and injecting the fragments to a part which should be treated, an effect higher than that of the injection of a single-cell suspension can be obtained (Wang et al., Cardiovasc Res. 2008 February 1; 77(3):515-24). Accordingly, such a use method can be applied also with respect to the sheet-shaped cell culture of the disclosure.

In an exemplary embodiment, the sheet-shaped cell culture of the disclosure can be substantially sterile. In an exemplary embodiment, the sheet-shaped cell culture of the disclosure can be sterile. In an exemplary embodiment, the sheet-shaped cell culture of the disclosure is not genetically manipulated. In another exemplary embodiment, the sheet-shaped cell culture of the disclosure is genetically manipulated. The genetic manipulation includes, without restriction, for example, introduction of a gene which can enhance the viability of the sheet-shaped cell culture, its engrafting ability, and function and/or a gene which is useful for treating a disease. Examples of the gene to be introduced can include, without restriction, cytokine genes such as HGF gene and VEGF gene.

Another aspect of the disclosure relates to a pharmaceutical composition containing the sheet-shaped cell culture of the disclosure.

The pharmaceutical composition of the disclosure may contain various additional components such as a pharmaceutically acceptable carrier, a component which enhances the viability of the sheet-shaped cell culture, its engrafting property, and/or function and another effective component which is useful for treating the target disease, in addition to the sheet-shaped cell culture of the disclosure. As the additional components, known components can be used, and one skilled in the art is familiar with the additional components. Moreover, the pharmaceutical composition of the disclosure can be combined with a component, which can enhance the viability of the sheet-shaped cell culture, its engrafting property, and/or function, another effective component which is useful for treating the target disease. In an exemplary embodiment, the pharmaceutical composition of the disclosure is for use in treating a disease associated with an abnormality of a tissue. The tissues and diseases to be treated are as described for the sheet-shaped cell culture of the disclosure.

Another aspect of the disclosure relates to a method for treating a disease associated with an abnormality of a tissue in a subject, containing administering an effective amount of the sheet-shaped cell culture of the disclosure or the pharmaceutical composition to a subject in need thereof. The tissues and the diseases to be treated by the treatment method of the disclosure are as described for the sheet-shaped cell culture of the disclosure. Also, in the treatment method of the disclosure, a component which can enhance the viability of the sheet-shaped cell culture, its engrafting property, and/or function, another effective component which is useful for treating the target disease can be combined with the sheet-shaped cell culture of the disclosure or the pharmaceutical composition.

The treatment method of the disclosure may further contain a step of producing a sheet-shaped cell culture according to the production method of the disclosure. The treatment method of the disclosure may further contain a step of collecting cells or a tissue serving as a source of cells for producing the sheet-shaped cell culture from a subject, before the step of producing the sheet-shaped cell culture. In an exemplary embodiment, the subject from which the cells or the tissue serving as a source of the cells is collected is the same individual as the subject treated by administration of the sheet-shaped cell culture or the pharmaceutical composition. In another embodiment, the subject from which the cells or the tissue serving as a source of the cells is collected is a different individual of the same species as the subject treated by administration of the sheet-shaped cell culture or the pharmaceutical composition. In another exemplary embodiment, the subject from which the cells or the tissue serving as a source of the cells is collected is an individual of a different species from that of the subject treated by administration of the sheet-shaped cell culture or the pharmaceutical composition.

In the disclosure, the term "subject" means any individual of a living thing, preferably an animal, further preferably a mammal, further preferably a human individual. In the disclosure, the subject may be healthy or may have any disease, but in case where the treatment of a disease associated with an abnormality of a tissue is planned, the subject having the disease or having the risk of developing the disease.

The term "treatment" can include all kinds of medically acceptable preventive and/or therapeutic intervention for the purpose of healing, remission, or prevention of a disease. For example, the term "treatment" can include medically acceptable intervention with various purposes including delaying or stopping of the progress of a disease associated with an abnormality of a tissue, regression or elimination of a lesion, prevention of the onset of the disease, and the prevention of the recurrence of the disease.

In the disclosure, the effective amount can be, for example, an amount which can help prevent the onset or recurrence of a disease, help reduce a symptom or delay or stop the progress (for example, the size or weight of the sheet-shaped cell culture) and is preferably an amount which prevents the onset and recurrence of the disease or cures the disease. Also, an amount which does not cause any adverse effect exceeding the advantages of the administration can be preferable. The amount can be suitably determined, for example, through a test using an experimental animal such as a mouse, a rat, a dog or a pig or a disease model animal, and such a test method is known to one skilled in the art. In addition, the size of the tissue lesion to be treated may be an important index for determining the effective amount.

The administration method can be direct application to a tissue, but when fragments of the sheet-shaped cell culture are used, the sheet-shaped cell culture may be administered through various routes through which administration by injection can be performed, such as intravenous, intramuscular, subcutaneous, local, intraarterial, intraportal, intraventricular and intraperitoneal routes.

The frequency of administration can be, for example, once per treatment, but several administrations can also be performed when the desired effect is not obtained.

The disclosure is explained in more detail referring to the following examples, but the examples are specific examples of the disclosure and the disclosure should not be restricted to the examples.

EXAMPLE 1

Cryopreserved human skeletal myoblasts (derived from a human skeletal muscle sample) were thawed at 37° C. and washed twice using a buffer containing 0.5% serum albumin. In a culture medium containing 20% serum, $5 \times 10^6$ to $5 \times 10^7$ cells were suspended, and the cells were seeded to a flask and then cultured for two to three days.

A culture medium containing 20% serum was added to UpCell (3.5 cm dish or 24-well multiwell, CellSeed Inc.) until the culture surface was completely covered, and the UpCell® was treated in an environment at 37° C. of 5% $CO_2$ for three hours to three days. After the treatment, the culture medium added was discarded.

The cultured cells were recovered, suspended in a culture medium containing 20% serum and seeded to the treated UpCell at a density of 2 to $20 \times 10^5$ cells/cm², and sheet-formation cultivation was carried out in an environment at 37° C. of 5% $CO_2$ for about a day.

EXAMPLE 2

In a culture medium containing 20% serum, $5 \times 10^6$ to $5 \times 10^7$ human skeletal myoblasts (derived from a human skeletal muscle sample) were suspended, and the cells were seeded to a flask and then cultured for two to three days. After recovering the cultured cells, the cells were suspended in a storage solution for freezing cells (a basal medium containing 10% DMSO) at a concentration of 1 to $5 \times 10^7$ cells/mL and cryopreserved in a liquid nitrogen tank.

A culture medium containing 20% serum was added to UpCell (3.5 cm dish or 24-well multiwell, CellSeed Inc.) until the culture surface was completely covered, and the UpCell® was treated in an environment at 37° C. of 5% $CO_2$ for three hours to three days. After the treatment, the culture medium added was discarded.

The cryopreserved skeletal myoblasts were thawed at 37° C. and washed twice using a buffer containing 0.5% serum albumin. The cells washed were suspended in a culture medium containing 20% serum and seeded to the treated UpCell® at a density of 2 to $20 \times 10^5$ cells/cm², and sheet-formation cultivation was carried out in an environment at 37° C. of 5% $CO_2$ for about a day.

EXAMPLE 3

Figure 1:
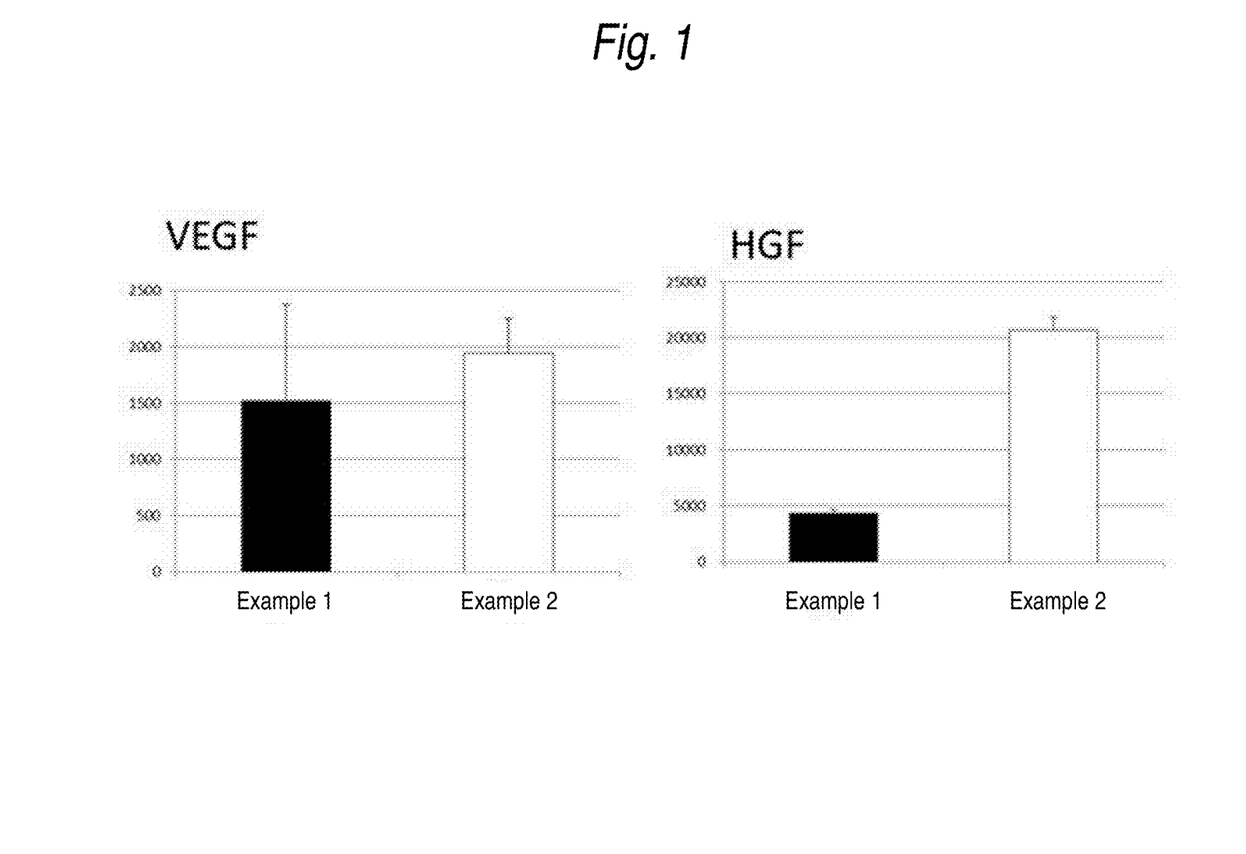
FIG. 1 is a graph showing the concentrations of VEGF and HGF secreted into culture solutions in the sheet-formation cultivation step in accordance with an exemplary embodiment.

After the sheet-formation cultivation in example 1 or example 2, all of the culture supernatants were recovered, and the concentrations of the cytokines (VEGF and HGF) produced in the culture supernatants were measured by ELISA (n=3). The measurement was carried out using Human VEGF Quantikine ELISA Kit (R&D systems, catalogue No. DVE00) and RayBio® Human HGF ELISA Kit (RayBiotech, Inc., catalogue No. ELH-HGF-001) in accordance with the manuals of the manufacturers. From the results shown in FIG. 1, it can be seen that VEGF and HGF are produced during the sheet-formation cultivation in both of the production methods of Example 1 and Example 2. The production amounts were higher in the production method of Example 2.

EXAMPLE 4

Figure 2:
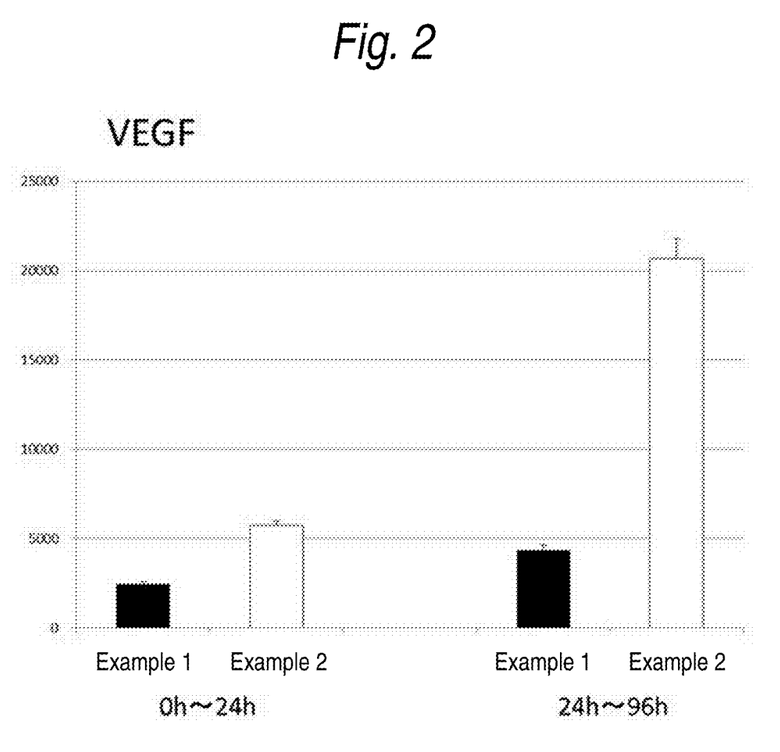
FIG. 2 is a graph showing the concentrations of VEGF secreted by sheet-shaped cell cultures after production into culture solutions in accordance with an exemplary embodiment.
Figure 3:
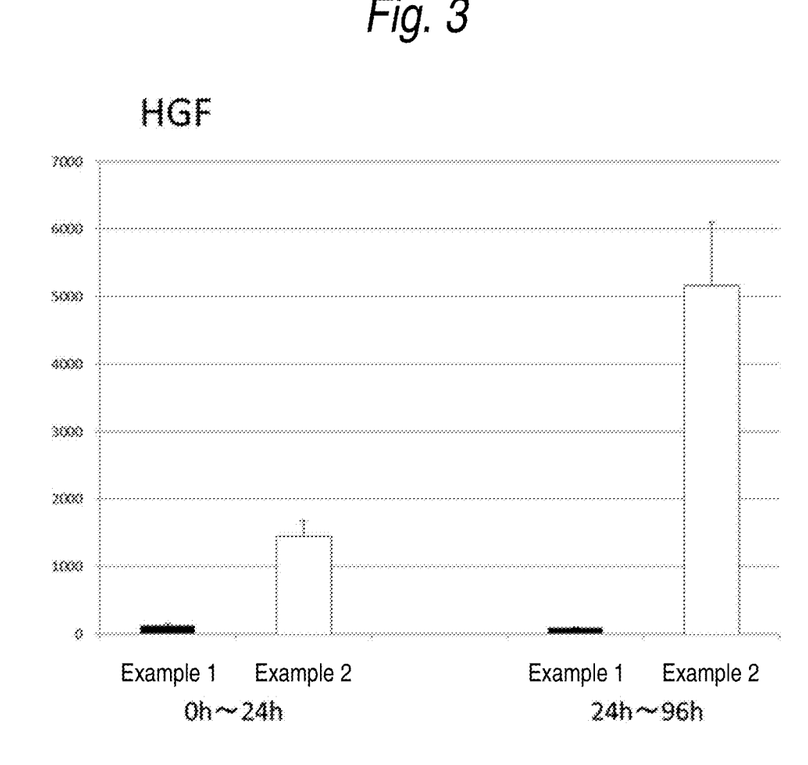
FIG. 3 is a graph showing the concentrations of HGF secreted by sheet-shaped cell cultures after production into culture solutions in accordance with an exemplary embodiment.

Sheet-shaped cell cultures formed in UpCell®(24-well multiwell, CellSeed Inc.) in accordance with the method of example 1 or example 2 were peeled off by thermal treatment and washed with HBSS(+). Then, 400 μL of an MCDB medium containing 2.5% FBS was added to each well, followed by cultivation in a $CO_2$ incubator for about 24 hours. After the cultivation, all of the supernatants were recovered, and the concentrations of the cytokines (VEGF and HGF) produced in the culture supernatants were measured by ELISA as in example 3. To the wells from which the supernatants were recovered, 400 μL of an MCDB medium containing 2.5% FBS was added again, followed by cultivation in a $CO_2$ incubator for 48 hours. After the cultivation, all of the supernatants were recovered, and the concentrations of the cytokines (VEGF and HGF) produced in the culture supernatants were measured by ELISA as in example 3. From the results shown in FIGS. 2 and 3, it can be seen that the sheet-shaped cell cultures produced by both of the production methods of Examples 1 and 2 produce VEGF and HGF and that the production continues for as long as 96 hours. In addition, the production amounts were higher with the sheet-shaped cell culture produced by the production method of Example 2.

EXAMPLE 5

Cryopreserved human mesenchymal stem cells are thawed at 37° C. and washed twice using a buffer containing 0.5% serum albumin. In a culture medium containing serum, $5 \times 10^6$ to $5 \times 10^7$ cells are suspended, and the cells are seeded to a flask and then cultured for two to three days.

A culture medium containing serum is added to UpCell® (3.5 cm dish or 24-well multiwell, CellSeed Inc.) until the culture surface is completely covered, and the UpCell® is treated in an environment at 37° C. of 5% $CO_2$ for three hours to three days. After the treatment, the culture medium added is discarded.

The cultured cells are recovered, suspended in a culture medium containing serum and seeded to the treated UpCell® at a density of 2 to $20 \times 10^5$ cells/$cm^2$, and sheet-formation cultivation is carried out in an environment at 37° C. of 5% $CO_2$ for about a day.

EXAMPLE 6

In a culture medium containing serum, $5 \times 10^6$ to $3 \times 10^7$ human mesenchymal stem cells are suspended, and the cells are seeded to a flask and then cultured for two to three days. After recovering the cultured cells, the cells are suspended in a storage solution for freezing cells (a basal medium containing 10% DMSO) at a concentration of 1 to $5 \times 10^7$ cells/mL and cryopreserved in a liquid nitrogen tank.

A culture medium containing serum is added to UpCell® (3.5 cm dish or 24-well multiwell, CellSeed Inc.) until the culture surface is completely covered, and the UpCell® is treated in an environment at 37° C. of 5% $CO_2$ for three hours to three days. After the treatment, the culture medium added is discarded.

The cryopreserved cells are thawed at 37° C. and washed twice using a buffer containing 0.5% serum albumin. The cells washed are suspended in a culture medium containing serum and seeded to the treated UpCell® at a density of 2 to $10 \times 10^5$ cells/$cm^2$, and sheet-formation cultivation is carried out in an environment at 37° C. of 5% $CO_2$ for about a day.

EXAMPLE 7

Cryopreserved human cardiac muscle cells are thawed at 37° C. and washed twice using a buffer containing 0.5% serum albumin. In a culture medium containing serum, $5 \times 10^6$ to $3 \times 10^7$ cells are suspended, and the cells are seeded to a flask and then cultured for two to three days.

A culture medium containing serum is added to UpCell® (3.5 cm dish or 24-well multiwell, CellSeed Inc.) until the culture surface is completely covered, and the UpCell® is treated in an environment at 37° C. of 5% $CO_2$ for three hours to three days. After the treatment, the culture medium added is discarded.

The cultured cells are recovered, suspended in a culture medium containing serum and seeded to the treated UpCell at a density of 2 to $20 \times 10^5$ cells/$cm^2$, and sheet-formation cultivation is carried out in an environment at 37° C. of 5% $CO_2$ for about a day.

EXAMPLE 8

In a culture medium containing serum, $5 \times 10^6$ to $3 \times 10^7$ human cardiac muscle cells are suspended, and the cells are seeded to a flask and then cultured for two to three days. After recovering the cultured cells, the cells are suspended in a storage solution for freezing cells (a basal medium containing 10% DMSO) at a concentration of 1 to $5 \times 10^7$ cells/mL and cryopreserved in a liquid nitrogen tank.

A culture medium containing serum is added to UpCell® (3.5 cm dish or 24-well multiwell, CellSeed Inc.) until the culture surface is completely covered, and the UpCell® is treated in an environment at 37° C. of 5% $CO_2$ for three hours to three days. After the treatment, the culture medium added is discarded.

The cryopreserved cardiac muscle cells are thawed at 37° C. and washed twice using a buffer containing 0.5% serum albumin. The cells washed are suspended in a culture medium containing serum and seeded to the treated UpCell® at a density of 2 to $20 \times 10^5$ cells/$cm^2$, and sheet-formation cultivation is carried out in an environment at 37° C. of 5% $CO_2$ for about a day.

EXAMPLE 9

In a culture medium containing serum, $1 \times 10^6$ to $3 \times 10^7$ human mesenchymal stem cells were suspended, and the cells were seeded to a flask and then cultured for two to three days. After recovering the cultured cells, the cells were suspended in a storage solution for freezing cells (a basal medium containing 10% DMSO) at a concentration of 1 to 5×10⁶ cells/mL and cryopreserved in a liquid nitrogen tank.

A culture medium containing serum was added to UpCell® (48-well multiwell, CellSeed Inc.) until the culture surface was completely covered, and the UpCell was treated in an environment at 37° C. of 5% $CO_2$ at normal pressure (atmospheric pressure) for three hours to three days as in Examples 1, 2 and 5 to 8. After the treatment, the culture medium added was discarded.

Figure 4:
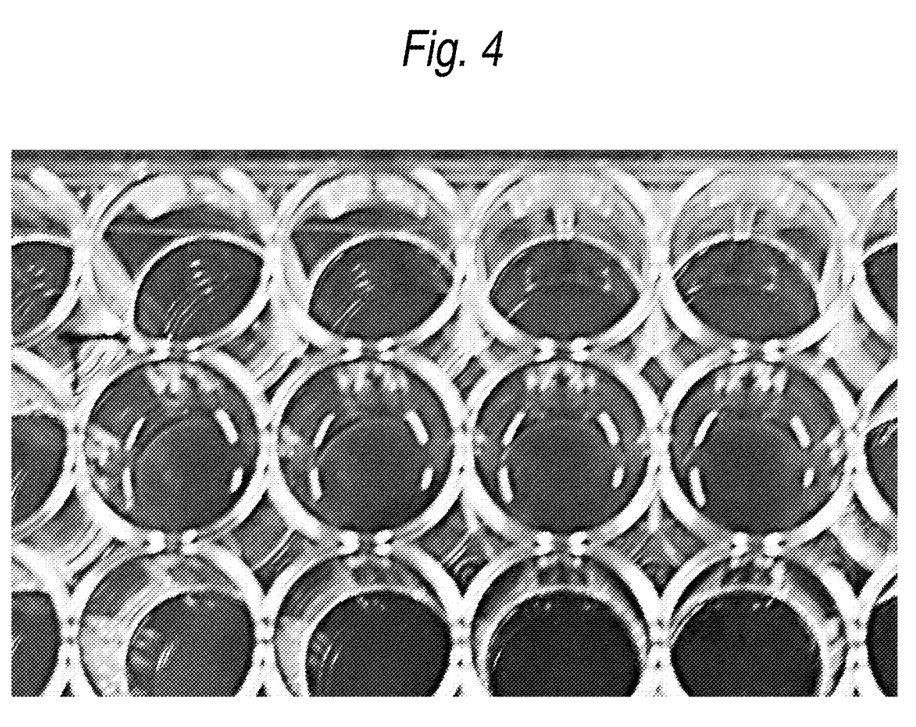
FIG. 4 is a photographic figure showing the mesenchymal stem sheet-shaped cell cultures produced by the production method of example 9, and wherein sheet-shaped cell cultures are observed in the four successive wells in the middle of the photograph figure.

The cryopreserved cells were thawed at 37° C. and washed twice using a buffer containing 0.5% serum albumin. The cells washed were suspended in a culture medium containing serum and seeded to the treated UpCell® at a density of 2 to 20×10⁵ cells/cm², and sheet-formation cultivation was carried out in an environment at 37° C. of 5% $CO_2$ at normal pressure (atmospheric pressure) for about a day as in Examples 1, 2 and 5 to 8. As shown in FIG. 4, the sheet-shaped cell cultures produced had homogeneous white color, and no defect was observed in an appearance test.

The detailed description above describes a method for producing a sheet-shaped cell culture. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A method for producing a sheet-shaped cell culture, comprising:
   proliferating myoblast cells;
   freezing the proliferated myoblast cells;
   thawing the frozen myoblast cells;
   forming a sheet-shaped cell culture with the thawed myoblast cells on a culture substrate by seeding the myoblast cells on the culture substrate at a density at which the cells can form a sheet-shaped cell culture substantially without any proliferation on the culture substrate, and wherein the myoblast cells are not proliferated between the freezing of the myoblast cells and the forming of the sheet-shaped cell culture; and
   removing the sheet-shaped cell culture from the culture substrate.

2. The method according to claim 1, comprising:
   recovering the sheet-shaped cell culture after the forming of the sheet-shaped cell culture, and wherein the thawing the myoblast cells is carried out within 48 hours before the recovering of the sheet-shaped cell culture.

3. The method according to claim 1, comprising:
   washing the cells after the thawing of the frozen myoblast cells and before the forming of the sheet-shaped cell culture.

4. The method according to claim 1, comprising:
   freezing the myoblast cells in the presence of a cryoprotectant.

5. The method according to claim 1, wherein the myoblast cells are human skeletal myoblast cells.

6. The method according to claim 1, further comprising:
   freezing the myoblast cells to at least a temperature of −80° C. at a rate of −0.46° C/minute.

7. The method according to claim 1, wherein the sheet-shaped cell culture has at least two times an amount of vascular endothelial growth factor (VEGF) 24 hours after seeding the sheet-shaped cell culture with the thawed myoblast cells as compared to an amount of VEGF present in a second sheet-shaped cell culture 24 hours after seeding wherein the second sheet-shaped cell culture is produced by a method that uses identical culture conditions except that the myoblast cells are proliferated between the steps of thawing of frozen myoblast cells and seeding the cells to form the sheet-shaped cell culture; and wherein the myoblast cells are skeletal myoblast cells.

8. A method for treating a disease associated with an abnormality of a tissue in a subject, comprising:
   producing a sheet-shaped cell culture, comprising:
      proliferating myoblast cells;
      freezing the proliferated myoblast cells;
      thawing the frozen myoblast cells;
      forming a sheet-shaped cell culture with the thawed myoblast cells on a culture substrate by seeding the myoblast cells on the culture substrate at a density at which the cells can form a sheet-shaped cell culture substantially without any proliferation on the culture substrate, and wherein the myoblast cells are not proliferated between the freezing of the myoblast cells and the forming of the sheet-shaped cell culture; and
      removing the sheet-shaped cell culture from the culture substrate; and
   administering an amount of the produced sheet-shaped cell culture to the subject, wherein the myoblast cell are autologous cells or allogeneic cells.

9. The method according to claim 8, wherein the myoblast cells are autologous cells.

10. The method according to claim 8, further comprising administering an amount of the sheet-shaped cell culture to a subject suffering from one or more of the following:
    an ischemic heart disease, a cardiac disease, or a muscular disease.

11. The method according to claim 10, wherein the ischemic heart disease is angina pectoris or myocardial infarction, the cardiac disease is a myocardiopathy, a myocardial infarction and cardiac injury, or cardiomyopathy, and the muscular disease is muscle damage or muscle inflammation.

12. The method according to claim 8, comprising:
    selecting the tissue from a group consisting of a cardiac muscle, a cornea, a retina, an esophagus, skin, a joint, cartilage, a liver, a pancreas, a gingiva, a kidney, a thyroid gland, a skeletal muscle and a middle ear.

13. The method according to claim 8, comprising:
    selecting the disease from a group consisting of a cardiac disease, a corneal disease, a retinal disease, an esophageal disease, a skin disease, a joint disease, a cartilage disease, a liver disease, a pancreatic disease, a dental disease, a renal disease, a thyroid disease, a muscular disease and a middle ear disease.

* * * * *